(12) United States Patent
Hossainy et al.

(10) Patent No.: US 9,808,362 B2
(45) Date of Patent: Nov. 7, 2017

(54) STENT FABRICATED FROM POLYMER COMPOSITE TOUGHENED BY A DISPERSED PHASE

(71) Applicant: Abbott Cardiovascular Systems Inc., Santa Clara, CA (US)

(72) Inventors: Syed F. A. Hossainy, Hayward, CA (US); David C. Gale, Kennesaw, GA (US); Stephen Dirk Pacetti, San Jose, CA (US); Bin Huang, Pleasanton, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 14/712,647

(22) Filed: May 14, 2015

(65) Prior Publication Data

US 2015/0351942 A1    Dec. 10, 2015

Related U.S. Application Data

(62) Division of application No. 11/827,180, filed on Jul. 10, 2007, now Pat. No. 9,089,627.

(60) Provisional application No. 60/830,211, filed on Jul. 11, 2006.

(51) Int. Cl.
*A61F 2/86* (2013.01)
*A61L 31/10* (2006.01)
*A61L 31/12* (2006.01)

(52) U.S. Cl.
CPC ............ *A61F 2/86* (2013.01); *A61L 31/10* (2013.01); *A61L 31/129* (2013.01); *A61F 2210/0076* (2013.01); *A61F 2230/0069* (2013.01)

(58) Field of Classification Search
None
See application file for complete search history.

(56) References Cited

U.S. PATENT DOCUMENTS

| | | | |
|---|---|---|---|
| 5,713,920 A * | 2/1998 | Bezwada | A61L 17/105 528/357 |
| 6,228,954 B1 * | 5/2001 | Kaplan | A61B 17/80 525/411 |
| 2004/0215315 A1 * | 10/2004 | Jones | A61F 2/958 623/1.11 |

* cited by examiner

*Primary Examiner* — Dennis Heyer
(74) *Attorney, Agent, or Firm* — Squire Patton Boggs (US) LLP

(57) ABSTRACT

Stents fabricated from polymer composites toughened by a dispersed phase are disclosed.

4 Claims, 2 Drawing Sheets

STENT FABRICATED FROM POLYMER COMPOSITE TOUGHENED BY A DISPERSED PHASE

CROSS REFERENCE TO RELATED APPLICATION

This application is a divisional of U.S. patent application Ser. No. 11/827,180 filed Jul. 10, 2007 which claims the benefit of U.S. Patent Application No. 60/830,211 which was filed on Jul. 11, 2006, both of which are incorporated by reference herein.

BACKGROUND OF THE INVENTION

Field of the Invention

This invention relates to a stent fabricated at least in part from a polymer composite toughened by a dispersed polymer phase.

Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a constraining member such as a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. This service life for a biodegradable stent is the length of time needed to support the vessel to prevent vessel recoil and negative remodeling. For example, a radially directed force may tend to cause a stent to recoil inward. Generally, it is desirable to minimize recoil. In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. In other embodiments, the scaffolding can be formed from machining, or cutting a pattern out of tubing. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

Potential problems with biodegradable polymeric implantable medical devices, such as stents, include insufficient toughness and slow degradation rate.

SUMMARY OF THE INVENTION

Various embodiments of the present invention include a stent comprising a body fabricated from a bioabsorbable polymer composite, the polymer composite comprising: a high toughness polymer dispersed within a matrix polymer, the matrix polymer being glassy at physiological conditions, wherein the high toughness polymer enhances the fracture toughness of the composite at physiological conditions.

Further embodiments of the present invention include a stent comprising a composite layer formed from a bioabsorbable polymer composite, the polymer composite comprising: a high toughness polymer dispersed within a matrix polymer, the matrix polymer being glassy at physiological conditions, wherein the high toughness polymer enhances the fracture toughness of the composite at physiological conditions.

DETAILED DESCRIPTION OF THE INVENTION

Various embodiments of the present invention include a stent fabricated at least in part from a polymer-polymer composite that includes a dispersed polymer phase. The dispersed phase tends to enhance the toughness of the composite.

Embodiments of the present invention relate to implantable medical devices including, but is not limited to, self-expandable stents, balloon-expandable stents, stent-grafts, other expandable tubular devices for various bodily lumen or orifices. Such devices can be designed for the localized delivery of a therapeutic agent. A medicated implantable medical device may be constructed by coating the device or substrate with a coating material containing a therapeutic agent. The substrate of the device may also contain a therapeutic agent.

Figure 1A:
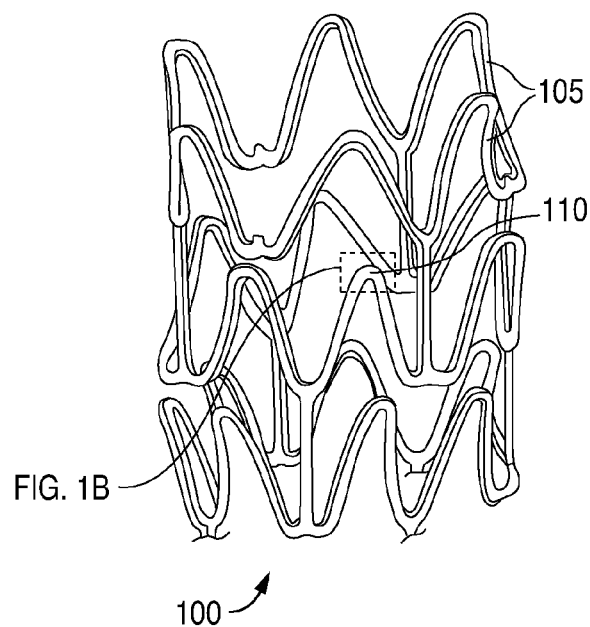
FIG. 1A depicts a view of a stent.

FIG. 1A depicts a view of a stent 100. In some embodiments, a stent may include a pattern or network of interconnecting structural elements 105. Stent 100 may be formed from a tube (not shown). The pattern of structural elements 105 can take on a variety of patterns. The structural pattern of the device can be of virtually any design. The embodiments disclosed herein are not limited to stents or to the stent pattern illustrated in FIG. 1A. The embodiments are easily applicable to other patterns and other devices. The variations in the structure of patterns are virtually unlimited. A stent such as stent 100 may be fabricated from a tube by forming a pattern with a technique such as laser cutting or chemical etching.

An implantable medical device can be made partially or completely from a biodegradable, bioabsorbable, biostable polymer, or a combination thereof. A polymer for use in fabricating an implantable medical device can be biostable, bioabsorbable, biodegradable or bioerodible. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and absorption of the polymer can be caused by, for example, hydrolysis and metabolic processes.

Stents are typically subjected to stress during use. "Use" includes manufacturing, assembling (e.g., crimping a stent on balloon), delivery of a stent through a bodily lumen to a treatment site, deployment of a stent at a treatment site, and treatment after deployment. Both the underlying scaffolding or substrate and the coating experience stress that result in strain in the substrate and coating. In particular, localized portions of the stent's structure undergo substantial deformation, such as at the apex regions of bending elements and experience relatively high stress and strain during crimping, expansion, and after expansion of the stent.

As discussed above, it is important for a stent body or scaffolding to have high radial strength and stiffness so that it can a support a lumen. Some crystalline or semi-crystalline polymers that are glassy or have a Tg above body temperature are particularly attractive as stent materials due to their strength and stiffness. Some of these polymers that may be suitable for implantable medical devices such as stents have potential shortcomings. One shortcoming of such polymers is that their toughness can be lower than desired, in particular, for use in stent applications. For example, polymers such as poly(L-lactide) (PLLA) are stiff and strong, but tend to be brittle under physiological conditions. Physiological conditions refer to conditions that an implant is exposed to within a human body. Physiological conditions include, but are limited to, human body temperature, approximately 37° C. These polymers can exhibit a brittle fracture mechanism at these conditions in which there is little or no plastic deformation prior to failure. As a result, a stent fabricated from such polymers can have insufficient toughness for the range of use of a stent.

As discussed above, a medicated implantable medical device, such as a stent, may be fabricated by coating the surface of a stent with a drug. For example, a device can have a coating including a drug dispersed in a polymeric carrier disposed over a substrate of the stent. Such polymer-based coatings may be particularly vulnerable to mechanical instability during use of a stent. Such mechanical instability for coatings can include fracture and detachment from a substrate, for exampling, peeling. Some polymers may be susceptible to such mechanical instability due to insufficient toughness at high deformations. Thus, it is important for a polymer-based coating to be tough and have a high resistance to cracking in the range of deformations that occur during crimping, during deployment of a stent, and after deployment.

Furthermore, some biodegradable polymers have a degradation rate that is slower than desired for certain stent treatments. As a result, the degradation time of a stent made from such polymers can be longer than desired. For example, a stent made from a semicrystalline polymer such as PLLA can have a degradation time between about two and three years. In some treatment situations, a shorter degradation time is desirable, for example, less than a year.

One way to form a tougher polymeric material from a brittle polymer is by making a composite including the brittle polymer and another polymer that has a higher fracture toughness than the brittle polymer. The higher toughness polymer should also be immiscible with or form a separate phase from the brittle polymer. For example, the higher toughness polymer can be dispersed as discrete phase domains within the matrix polymer. The fracture toughness of the composite is increased since the dispersed phase can absorb energy arising from stress imparted to a part made from the composite. The increase in the fracture toughness can be enhanced by increasing the adhesion of the dispersed phase with the continuous polymer phase. To ensure good energy transfer between interfaces of the phases, it is important that there be sufficient bonding or adhesion between the phases. See, Y. Wang, etc. Journal of Polymer Science Part A: Polymer Chemistry, 39, 2001, 2755-2766.

Certain embodiments of the present invention include a stent having a body or scaffolding fabricated from a bioabsorbable polymer composite. In some embodiments, the polymer composite includes a high toughness polymer dispersed within a matrix polymer. The high toughness polymer can be a dispersed phase within the matrix polymer which can be a continuous polymer phase. The matrix polymer may be glassy at physiological conditions. In an embodiment, the high toughness polymer may have a lower modulus than the glassy matrix polymer.

In some embodiments, a stent body can refer to a stent scaffolding with an outer surface to which no coating or layer of material different from that of which the device is manufactured has yet been applied. If the body is manufactured by a coating process, the stent body can refer to a state prior to application of optional additional coating layers of different material. By "outer surface" is meant any surface however spatially oriented that is in contact with bodily tissue or fluids. A stent body can refer to a stent scaffolding formed by laser cutting a pattern into a tube or a sheet that has been rolled into a cylindrical shape.

In some embodiments, a majority, substantially all, or all of the stent body or scaffolding can be made from the composite. Substantially all of the body can refer to greater than 90%, 95%, or greater than 99% of the body.

Additionally, the matrix polymer is stronger and stiffer than the high toughness polymer and is primarily or completely responsible for providing strength required to support the walls of a bodily lumen when the stent is deployed at a treatment site. In such embodiments, the high toughness polymer enhances the fracture toughness of the composite at physiological conditions. Thus, the high toughness polymer reduces or prevents formation of cracks during use of the stent. In some embodiments, the interfacial adhesion of the dispersed phase with the matrix or continuous polymer phase is high enough to allow for the dispersed phase to increase the fracture toughness of the composite during use of a stent. "Use" includes manufacturing, assembling (e.g., crimping a stent on balloon), delivery of a stent through a bodily lumen to a treatment site, and deployment of a stent at a treatment site. In such embodiments, the interfacial adhesion between the dispersed phase of the high toughness polymer and the matrix polymer is high enough such that when a stress is placed upon the interface during use of a stent, the high toughness polymer fails before an interfacial bond between the phases. In other such embodiments, the interfacial adhesion between the dispersed phase of the high toughness polymer and the matrix polymer is greater than the strength of the high toughness polymer. In additional embodiments, the interfacial adhesion between the dispersed phase of the high toughness polymer and the matrix polymer is at least 10% of the strength of the high toughness polymer.

Figure 1B:
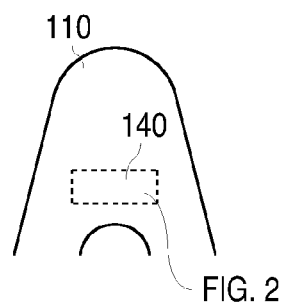
FIG. 1B depicts a section of a structural element from the stent depicted in FIG. 1A.
Figure 2:
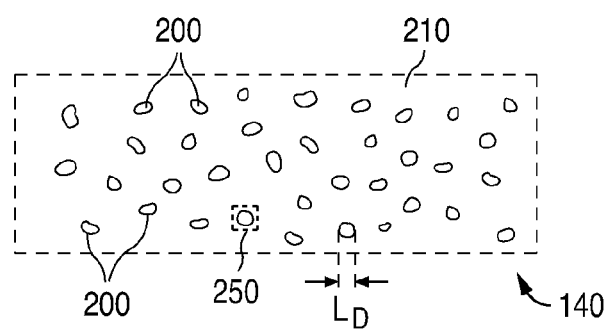
FIG. 2 depicts a schematic close-up view of the section depicted in FIG. 1B.

FIG. 1B depicts a section of a segment 110 of strut 105 from the stent depicted in FIG. 1A. FIG. 2 depicts a microscopic schematic view of a portion 140 of segment 110 of a strut as depicted in FIG. 1B. Portion 140 includes a dispersed phase with a plurality of discrete polymer phase regions 200 dispersed within a continuous polymer phase 210. Discrete phase regions include a polymer that is tougher than the polymer of the continuous polymer phase. $L_D$ is a characteristic dimension of discrete phase regions 200.

In further embodiments of the present invention, a stent can include layers of bioabsorbable composite with a high toughness polymer dispersed within a matrix polymer. In such embodiments, a composite layer can be therapeutic with a drug or active agent incorporated within the layer. In some embodiments, the composite layer can be formed above or over at least a portion of a stent body. The stent body can be polymeric, metallic, or a combination thereof. The high toughness polymer enhances the fracture toughness of the composite at physiological conditions which reduces or prevents fracture and detachment of the composite layer from a stent.

In some embodiments, the composite layer is a coating layer that may be formed above the stent body or scaffolding. The stent body is primarily or completely responsible for mechanical support of a bodily lumen when the stent is deployed. In an embodiment, the stent body or scaffolding can be composed of a polymer that allows the stent body to provide requisite mechanical support to a bodily lumen. In an embodiment, a stent body or scaffolding is composed of a strong, glassy polymer.

In some embodiments, the stent body or scaffolding is also composed of a composite, as described above. In this embodiment, the stent body composite can be stronger and stiffer than the composite coating layer. The coating layer can have a higher weight percent of high toughness polymer than the stent body composite. In certain embodiments, the high toughness polymer can be all or a majority of the composite of a layer over a stent body.

Figure 3:
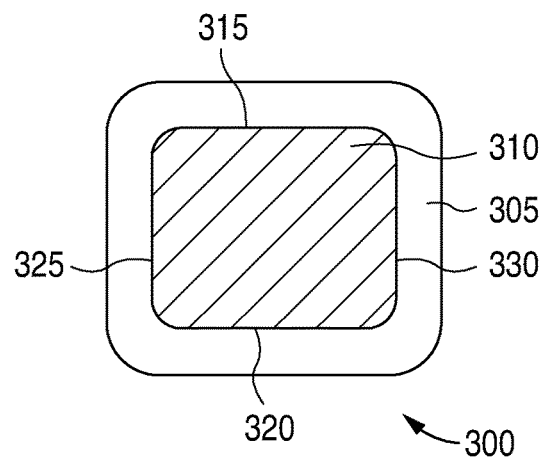
FIG. 3 depicts an axial cross-section of a strut showing a coating over a scaffolding or body.

In certain embodiments, a composite layer may be above all or a portion of a stent body or scaffolding. FIG. 3 depicts an axial cross-section of a strut 300 showing a coating 305 over a stent scaffolding or body 310. Coating 305 is above a luminal surface 315, abluminal surface 320, and sidewall surfaces 325 of body 310. In another embodiment, a composite layer can be topcoat layer disposed over polymer and drug coating layer. The topcoat layer can be used to control the drug release from the polymer and drug layer.

Figure 4:
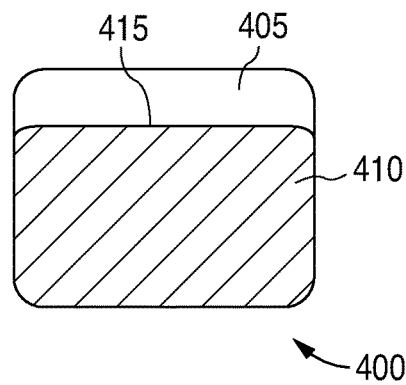
FIG. 4 depicts an exemplary axial cross-section of a strut with an abluminal composite layer over a luminal stent body layer.
Figure 5:
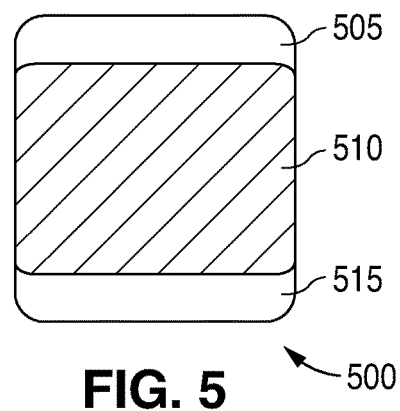
FIG. 5 depicts an exemplary axial cross-section of a strut with a stent body layer between a luminal composite layer and an abluminal composite layer.

In further embodiments, a stent can include structural elements having an abluminal luminal, or both abluminal and luminal composite layers. In one embodiment, a stent has an abluminal composite layer over a stent body polymer layer capable of providing mechanical support of a bodily lumen. In another embodiment, a stent has a luminal composite layer and an abluminal glassy polymer layer. In an additional embodiment, the stent has luminal and abluminal composite layers with a stent body layer between the abluminal and luminal composite layers. The stent body layer can be glassy polymer or a composite layer that can be different from the abluminal/luminal composite layer. In such embodiments, the stent body polymer layer is primarily or completely responsible for providing mechanical support to a bodily lumen when the stent is deployed. FIG. 4 depicts an exemplary axial cross-section of a strut 400 with a composite layer 405 over a luminal surface 415 of a stent body layer 410. FIG. 5 depicts an exemplary axial cross-section of a strut 500 with a stent body layer 510 between a luminal composite layer 505 and an abluminal composite layer 515.

In some embodiments, the matrix polymer of the composite is a crystalline or semicrystalline polymer having a degree of crystallinity greater than about 30%. Exemplary matrix polymers include PLLA, polyglycolide (PGA), poly (L-lactide-co-D,L-lactide), poly(L-lactide-co-glycolide), poly(L-lactide-co-caprolactone), poly(L-lactide-co-trimethylene carbonate), poly(ester amide) (PEA), or copolymers thereof.

In some embodiments, the high toughness polymer exhibits a rubbery or elastomeric behavior at physiological conditions. An "elastomeric" or "rubbery" polymer refers to a polymer that exhibits elastic deformation through all or most of a range of deformation. Such elastomeric properties provide the composite with a high fracture toughness during use of the stent. In some embodiments, the high toughness polymer has glass transition temperature (Tg) below body temperature. Additionally, the high toughness polymer may be completely or substantially amorphous.

In some embodiments, the high toughness polymer is rubbery, bioabsorbable or biodegradable, biocompatible polymer. Exemplary biodegradable polymers that are elastomeric or rubbery at physiological conditions include, but are not limited to, poly(butylene succinate) (PBS), poly-caprolactone (PCL), poly(trimethylene carbonate) (PTMC), poly(4-hydroxy butyrate) (PHB), aliphatic polyanhydrides, polyorthoesters, and polydioxanone (PDO). An exemplary commercial embodiment of PBS is Bionolle® 3000 from Showa Highpolymer Co. Ltd., Tokyo, Japan. In other embodiments, the high toughness polymer can be a random or alternating copolymer of the above polymer or other rubbery polymers.

The weight percent of the high toughness polymer in the composite can be adjusted to obtain a desired or optimal degree of fracture toughness. In particular, a weight percent of high toughness polymer can be selected to result in a selected maximum threshold number of cracks or no cracks in a stent body or coating layer upon crimping, deployment, or both. In addition, a weight percent of high toughness polymer can be selected to result in no or substantially no detachment of a coating layer upon crimping, deployment, or both. In addition, the amount of the high toughness polymer can be limited by desired or required radial strength of the stent. In some embodiments, the high toughness polymer can be at least 0.1, 1, 3, 5, 10, 20, 30, or 40 wt % of the composite.

An exemplary embodiment of a stent body or scaffolding can be fabricated from a composite including a blend of PBS dispersed within PLLA. The weight percent of PBS can be at least 20, 40, 60, 80 wt % or greater than 80 wt %. An exemplary embodiment of a coating for a stent body is a blend of PBS dispersed within PDLA with a weight percent of PBS of at least 20, 40, 60, 80 wt % or greater than 80 wt %.

In additional embodiments, the high toughness polymer is a random or alternating copolymer including elastomeric units and glassy polymer units. In other embodiments, the high toughness polymer can be a block copolymer including elastomeric blocks and glassy polymer blocks. The relative weight percent of the elastomeric and glassy polymer units or blocks can be adjusted to obtain desired properties of the polymer, such as, modulus, Tg, and elastomeric behavior. It is expected that as the weight percent of elastomeric units or blocks increase in the polymer, the modulus of the high toughness polymer decreases and the flexibility increases. Additionally, the weight percent of the elastomeric units or blocks can be adjusted so that the high toughness polymer is elastomeric at physiological conditions and/or the Tg of the high toughness polymer is below body temperature.

Exemplary elastomeric units include butylene succinate (BS), caprolactone (CL), trimethyl carbonate (TMC), 4-hydroxy butyrate (HB), and dioxanone (DO). Exemplary glassy polymer units include L-lactide (LLA), and glycolide (GA). Exemplary block copolymers that can be used as a high toughness polymer can include blocks of these elastomeric units and blocks of these glassy units.

In some embodiments, a random, alternating, or block high toughness copolymer can have glassy units or blocks that are the same as the matrix polymer. For example, the matrix polymer can be PLLA and the high toughness polymer can be P(LLA-co-TMC). In such embodiments, the adhesion of the dispersed phase to the matrix polymer can be enhanced due to the compatibility of the glassy polymer with the matrix polymer. In some embodiments, blocks or segments of the high toughness polymer can phase separate into the matrix polymer. It is believed that such phase separation increases the interfacial adhesion of the dispersed phase with the continuous phase.

Additionally, the weight percent of the glassy and elastomeric units or blocks of the high toughness polymer can be adjusted so that the high toughness polymer is immiscible with the matrix polymer. In some embodiments, the elastomeric units can be at least 0.1, 1, 3, 5, 10, 20, 30, 40 wt % or more than 40 wt % of the high toughness copolymer.

In an exemplary embodiment, a stent body can be composed of a PLLA matrix with dispersed 70/30 P(LLA-co-TMC) (70 wt % LLA and 30 wt % TMC). An exemplary coating or outer layer of a stent can be a poly(D,L-lactide) (PDLA) matrix with dispersed 70/30 P(DLA-co-TMC) (70 wt % DLA and 30 wt % TMC).

In some embodiments, the adhesion of the dispersed phase with the matrix or continuous polymer phase can be enhanced by including a compatibilizer in the composite. In general, a "compatibilizer" refers to an interfacial agent that modifies the properties of an immiscible polymer blend or composite which facilitates formation of uniform blend, and increases interfacial adhesion between the phases. Compatibilization refers to the process of modification of the interfacial properties in an immiscible polymer blend that results in formation of interphases (region of concentration gradient between phases) and stabilization of the morphology. In some embodiments, a compatibilizer can be a block copolymer including blocks that are miscible with the matrix polymer and blocks that are miscible with the high toughness polymer of the dispersed phase. In one such embodiment, the compatibilizer can include glassy blocks of the matrix polymer and elastomeric blocks of the high toughness polymer. In an exemplary embodiment, the matrix polymer can be PLLA, the high toughness polymer can be PTMC and the compatibilizer can be PLLA-b-PTMC.

In some embodiments, the high toughness polymer can have a faster degradation rate than the matrix polymer. As indicated above, a polymer, such as PLLA, can have a degradation rate that is slower than desired for certain stent treatments. The slow degradation rate is due at least in part to the crystallinity of a matrix polymer. The faster degradation rate of the high toughness polymer can be due at least in part to a lower degree of crystallinity or a higher percentage amorphous structure of the dispersed phase. The diffusion rate of fluids through an amorphous structure is generally faster than through a crystalline structure. The faster degrading, high toughness polymer increases water penetration and content in the dispersed phase and matrix polymer phase. The increased water penetration and content causes an increase in the degradation rate of the composite. As a result, the degradation time of a stent body or coating is decreased.

It is believed that when a device is placed under stress, the dispersed phase tends to absorb energy when a fracture starts to propagate through a structural element. Thus, crack propagation through the continuous phase may then be reduced, inhibited, or eliminated. As a result, fracture toughness of the polymer composite, and thus, the stent body or coating tends to be increased.

Generally, it is desirable for the dispersed phase to be uniformly or substantially uniformly dispersed throughout the polymer matrix to facilitate the increase in toughness. The more dispersed the dispersed phase, the greater is the increase in toughness. Additionally, the increase in toughness is related to the size of the discrete phase regions. The characteristic length of a discrete phase can be 1 nm to 100 nm, 100 nm to 500 nm, 500 nm to 1,000 nm, or greater than 1,000 nm.

In certain embodiments, the composite of a high toughness polymer and a matrix polymer can be formed by solution blending, melt blending, or a combination thereof. In some embodiments, a high toughness polymer and matrix polymer can be melt blended in a mixing apparatus such as an extruder. Representative examples of extruders include, but are not limited to, single screw extruders, intermeshing co-rotating and counter-rotating twin-screw extruders, and other multiple screw masticating extruders. The mixing in the extruder can be sufficient to disperse the high toughness polymer uniformly or relatively uniformly within the matrix polymer. Additionally, the mixing can also reduce the size of the discrete phase domains.

As indicated above, a stent body can be formed from a tube or a sheet. In some embodiments, a tube or sheet can be formed from the composite using an extruder or injection molding. The sheet can be rolled or bonded to form a tube. A stent body or scaffolding can then be formed from the composite tube by laser machining a stent pattern in the tube. In In further embodiments, a composite layer over a stent body or scaffolding can be formed by coating the stent body or scaffolding. In such embodiments, a coating layer may be formed by applying a coating material to a body of a stent. The coating material can be a polymer solution that includes the matrix polymer and high toughness polymer dissolved in solvent. The solution can further include a drug dispersed in the solution. The coating material may be applied to the stent body by immersing the stent in the coating material, by spraying the material onto the stent, or by other methods known in the art. The solvent in the solution is then removed, for example, by evaporation, leaving on the stent surfaces a polymer coating impregnated with the drug.

In another embodiment, a stent having a glassy polymer layer with abluminal, luminal, or both luminal and abluminal composite layers can be formed from a tube with composite layers. Such a tube can be formed by co-extruding the composite polymer with a polymer that will form a layer that provides mechanical support. A stent can be cut from the tube to form a layered stent. An active agent or drug can be included in the composite layers during extrusion. In some embodiments, a polymer solvent solution can be extruded at a temperature less than a temperature at which the active agent or drug degrades. For example, the coextrusion can be performed at a temperature below 80° C. or 100° C.

In alternative embodiments, an abluminal or luminal layer can by selectively coated on an abluminal or luminal surface of a stent body. In one embodiment, a controlled deposition system can be used that applies various substances only to certain targeted portions of a stent. A representative example of such a system, and a method of using the same, is described in U.S. Pat. No. 6,395,326 to Castro et al. Alternatively, a luminal or abluminal surface can be masked during the coating process to selectively coat an abluminal or luminal surface, respectively.

In general, representative examples of polymers that may be used in embodiments of the present invention include, but are not limited to, poly(N-acetylglucosamine) (Chitin), Chitosan, poly(3-hydroxyvalerate), poly(D,L-lactide-co-glycolide), poly(3-hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(L-lactide-co-glycolide); poly(D,L-lactide), poly(L-lactide-co-D,L-lactide), poly(L-lactide-co-caprolactone), poly(caprolactone), poly(trimethylene carbonate), polyethylene amide, polyethylene acrylate, poly(glycolic acid-co-trimethylene carbonate), poly(glycolide-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Additional representative examples of polymers that may be especially well suited for use in embodiments of the present invention include ethylene vinyl alcohol copolymer (commonly known by the generic name EVOH or by the trade name EVAL), poly(butyl methacrylate), poly(vinylidene fluoride-co-hexafluoropropylene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

For the purposes of the present invention, the following terms and definitions apply:

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting mobility.

"Stress" refers to force per unit area, as in the force acting through a small area within a plane. Stress can be divided into components, normal and parallel to the plane, called normal stress and shear stress, respectively. True stress denotes the stress where force and area are measured at the same time. Conventional stress, as applied to tension and compression tests, is force divided by the original gauge length.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force. For example, a material has both a tensile and a compressive modulus. A material with a relatively high modulus tends to be stiff or rigid. Conversely, a material with a relatively high toughness tends to be flexible. The modulus of a material depends on the molecular composition and structure, temperature of the material, amount of deformation, and the strain rate or rate of deformation. For example, below its Tg, a polymer tends to be brittle with a high modulus. As the temperature of a polymer is increased from below to above its Tg, its modulus decreases.

"Strain" refers to the amount of elongation or compression that occurs in a material at a given stress or load.

"Elongation" may be defined as the increase in length in a material which occurs when subjected to stress. It is typically expressed as a percentage of the original length.

"Toughness" is the amount of energy absorbed prior to fracture, or equivalently, the amount of work required to fracture a material. One measure of toughness is the area under a stress-strain curve from zero strain to the strain at fracture. Thus, a brittle material tends to have a relatively low toughness.

"Solvent" is defined as a substance capable of dissolving or dispersing one or more other substances or capable of at least partially dissolving or dispersing the substance(s) to form a uniformly dispersed solution at the molecular- or ionic-size level at a selected temperature and pressure. The solvent should be capable of dissolving at least 0.1 mg of the polymer in 1 ml of the solvent, and more narrowly at least 0.5 mg in 1 ml at the selected temperature and pressure, for example, ambient temperature and ambient pressure.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A balloon expandable stent mounted about a balloon disposed on a catheter, the stent comprising:
   a scaffold including a pattern of interconnecting structural elements,
   wherein the scaffold is fabricated from a blend of poly (L-lactide) (PLLA) matrix polymer, a random copolymer of poly(L-lactide-co-caprolactone), and a compatibilizer which is a block copolymer of poly(L-lactide) and polycaprolactone, and
   wherein the poly(L-lactide-co-caprolactone) random copolymer is at least 10 wt % of the blend and the caprolactone is at least 20 wt % of the poly(L-lactide-co-caprolactone) random copolymer and;
   a coating on the scaffold, wherein the coating comprises a drug dispersed within a polymeric carrier.

2. The stent of claim 1, wherein the poly(L-lactide-co-caprolactone) forms a dispersed phase within the PLLA matrix polymer.

3. The stent of claim 2, wherein a characteristic length of discrete phase regions of the dispersed phase is 100 nm to 1000 nm.

4. The stent of claim 1, wherein greater than 95% of the scaffold is made of the blend.

* * * * *